US012575890B2

(12) United States Patent
Jacobsen et al.

(10) Patent No.: US 12,575,890 B2
(45) Date of Patent: Mar. 17, 2026

(54) SYSTEMS AND METHODS FOR IMPROVED ELECTROMAGNETIC TRACKING

(71) Applicant: Medtronic Navigation, Inc., Louisville, CO (US)

(72) Inventors: Bradley W. Jacobsen, Erie, CO (US); Andrew J. Wald, Denver, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 17/455,163

(22) Filed: Nov. 16, 2021

(65) Prior Publication Data

US 2022/0183765 A1     Jun. 16, 2022

Related U.S. Application Data

(60) Provisional application No. 63/126,061, filed on Dec. 16, 2020.

(51) Int. Cl.
*A61B 34/20* (2016.01)
*A61B 34/00* (2016.01)
*A61B 90/00* (2016.01)

(52) U.S. Cl.
CPC .............. *A61B 34/20* (2016.02); *A61B 34/25* (2016.02); *A61B 90/37* (2016.02); *A61B 2034/2051* (2016.02)

(58) Field of Classification Search
None
See application file for complete search history.

(56) References Cited

U.S. PATENT DOCUMENTS 5,099,845 A * 3/1992 Besz ........................ A61B 5/06
                                                            324/207.17
2003/0055317 A1     3/2003 Taniguchi et al.
(Continued)

FOREIGN PATENT DOCUMENTS

EP         1 067 863        12/2005
EP         1891895 A1        2/2008
WO      2022133435 A1        6/2022

OTHER PUBLICATIONS

International Search Report and Written Opinion for International PCT Application No. PCT/US2021/072904, mailed Mar. 29, 2022, 18 pages.
(Continued)

*Primary Examiner* — Christopher Koharski
*Assistant Examiner* — Renee C Langhals
(74) *Attorney, Agent, or Firm* — Mueting Raasch Group

(57)             ABSTRACT
Tracking a pose of a portion of an anatomical structure using an inverted-direction electromagnetic navigation system may comprise generating a signal comprising a plurality of frequencies. The signal comprising the plurality of frequencies may be received at a transmitter coil array. The transmitter coil array comprises a plurality of transmitting micro coils. Each of the plurality of transmitting micro coils is coupled to a portion of an anatomical structure of a patient. In response to receiving the signal comprising the plurality of frequencies, an electromagnetic field may be generated at each of the plurality of transmitting micro coils based on the received signal. Each of the generated electromagnetic fields may be detected at a receiver coil array comprising at least one receiving coil. A pose of at least one of the plurality of transmitting micro coils may then be determined.

20 Claims, 5 Drawing Sheets

(56)                References Cited

U.S. PATENT DOCUMENTS

2004/0068178 A1      4/2004  Govari
2004/0171924 A1*     9/2004  Mire ...................... A61B 34/20
                                                              600/407
2008/0125646 A1*     5/2008  Govari .................. A61B 5/062
                                                              702/152
2008/0161680 A1*     7/2008  von Jako ............... G16H 50/50
                                                              600/407
2008/0228064 A1*     9/2008  Krueger ............... G01R 33/286
                                                              600/414
2009/0069671 A1      3/2009  Anderson
2009/0115406 A1      5/2009  Anderson et al.
2010/0106154 A1*     4/2010  Harlev .................. A61B 34/20
                                                              600/407
2010/0130853 A1      5/2010  Chandonnet et al.
2010/0249571 A1      9/2010  Jensen et al.
2013/0079790 A1      3/2013  Stein et al.
2013/0267833 A1*    10/2013  Schroeder ............... G01B 7/02
                                                              600/424
2014/0077811 A1*     3/2014  Lin .................. G01R 33/56509
                                                              324/309

2014/0228669 A1*     8/2014  Carter .................. A61N 1/0541
                                                              600/409
2014/0276010 A1*     9/2014  Anderson .............. A61B 90/39
                                                              600/424
2017/0023381 A1*     1/2017  Bertrand .............. G01D 5/2006
2019/0328272 A1     10/2019  Bredehoft et al.
2021/0330390 A1     10/2021  Bredehoft et al.
2021/0330391 A1     10/2021  Bredehoft et al.
2021/0330392 A1     10/2021  Bredehoft et al.
2022/0183765 A1      6/2022  Jacobsen et al.
2022/0241025 A1      8/2022  Jacobsen et al.

OTHER PUBLICATIONS

Sen H Tutkun et al: "Particle filtering to improve the dynamic accuracy of electromagnetic tracking", 2013 IEEE Sensors, IEEE, Nov. 3, 2013 (Nov. 3, 2013), pp. 1-4.
International Preliminary Report on Patentability, corresponding to PCT/US2021/072904, Date of Issuance of Report: Jun. 13, 2023.
Office Action issued in Europe for Application No. 21851775.3 dated Dec. 1, 2025.

* cited by examiner

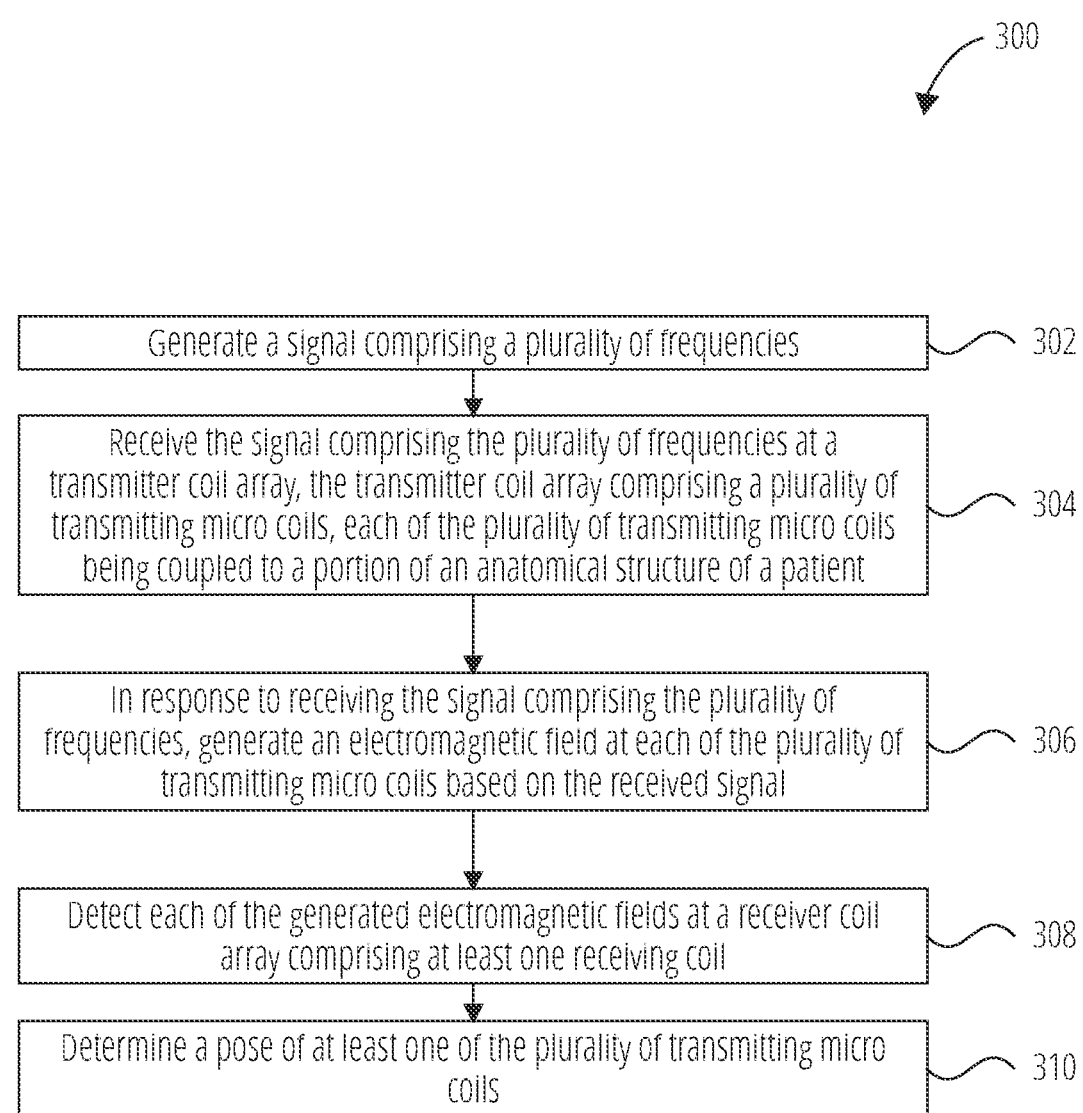

300

| Generate a signal comprising a plurality of frequencies | 302 |

Receive the signal comprising the plurality of frequencies at a transmitter coil array, the transmitter coil array comprising a plurality of transmitting micro coils, each of the plurality of transmitting micro coils being coupled to a portion of an anatomical structure of a patient — 304

In response to receiving the signal comprising the plurality of frequencies, generate an electromagnetic field at each of the plurality of transmitting micro coils based on the received signal — 306

Detect each of the generated electromagnetic fields at a receiver coil array comprising at least one receiving coil — 308

Determine a pose of at least one of the plurality of transmitting micro coils — 310

FIG. 3

400 network 410 user interface 412 output 414 input 416 communication channels 408 processors(s) 402 memory 404 executable component 406 volatile non-volatile

SYSTEMS AND METHODS FOR IMPROVED ELECTROMAGNETIC TRACKING

RELATED APPLICATIONS

This application claims priority to U.S. Provisional Application No. 63/126,061 filed on Dec. 16, 2020 and titled "INVERTED-DIRECTION, SPREAD-SPECTRUM SIGNALING ELECTROMAGNETIC NAVIGATION" which is hereby incorporated by reference in its entirety.

TECHNICAL FIELD

The present disclosure relates generally to devices and systems used to track a pose of one or more portions of a structure. More specifically, the present disclosure relates to an electromagnetic (EM) tracking system used to track the pose of vertebrae during spinal corrective surgery.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 3 illustrates a flowchart of a method associated with an inverted-direction electromagnetic navigation system in accordance with one embodiment.

DETAILED DESCRIPTION

Figure 1:
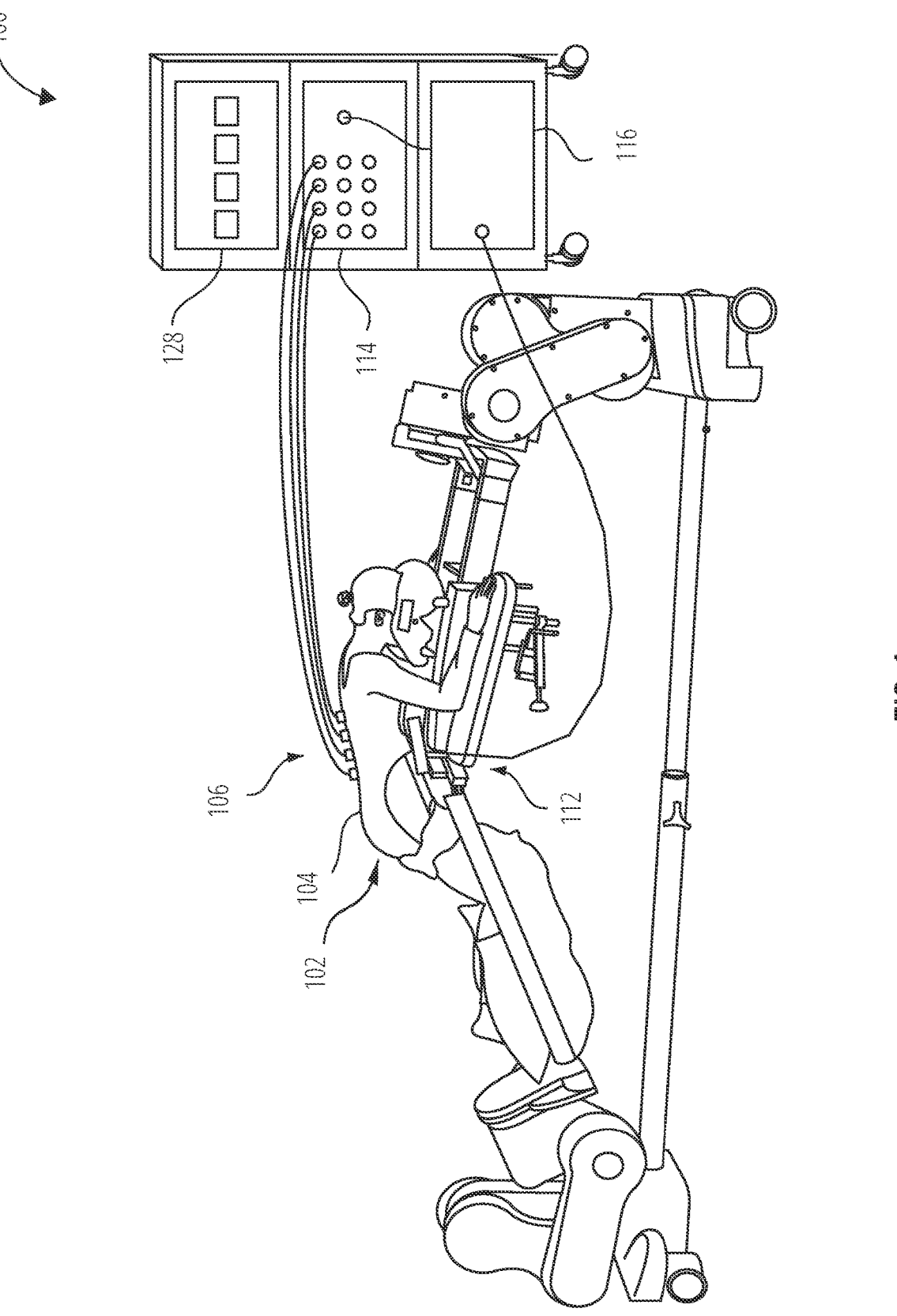
FIG. 1 illustrates an electromagnetic navigation system in accordance with one embodiment.

In certain instances, a corrective surgery may be performed on a patient to treat or correct an acute injury, a chronic injury, or a chronic disease (e.g., scoliosis) of an anatomical structure (e.g., spine) of a patient. For example, a corrective spinal surgical procedure may be performed to align displaced or misaligned vertebrae while retention implants or hardware are secured to the vertebrae. In such cases, an electromagnetic (EM) navigation (or tracking) system may be used to track a pose of a vertebra relative to an adjacent vertebra to facilitate adequate displacement and alignment of the spinal column. As used herein, pose is understood to include at least some tracked or navigated position coordinates (e.g. x, y, z) and/or orientation coordinates (e.g. roll, pitch, yaw). The EM navigation system may track a position and/or orientation, including six degree of freedom of motion (e.g. a three-dimensional position and a plurality, e.g. pitch, roll, and yaw orientation) of a tracked structure. The pose or position and/or orientation of the tracked structure, therefore, may be determined over time.

EM navigation systems often use macro-coil transmitters and mini-coil or micro-coil receivers as part of standard direction signaling. Notably, magnetic field sensors may also be used as receivers (i.e., in addition to, or in place of, coil receivers). Such magnetic field sensors may include, but are not limited to, fluxgates, Hall sensors, magnetoresistive sensors, optical sensors, and atomic sensors.

The large transmitters (i.e., macro-coil transmitters) of standard direction signaling emit magnetic fields and induce electric voltages over large volumes to navigate large ranges. As such, received signals must be balanced with both magnetic and conductive distortions. These distortions may be removed or reduced through various methods. In particular, conductive distortions may be removed by disclosed methods discussed in U.S. patent application Ser. No. 15/963,444 (titled POSITION DETERMINATION SYSTEM AND METHOD and filed Apr. 26, 2018); U.S. patent application Ser. No. 16/855,487 (titled SYSTEM AND METHOD FOR NAVIGATION and filed Apr. 22, 2020); U.S. patent application Ser. No. 16/855,521 (titled SYSTEM AND METHOD FOR NAVIGATION and filed Apr. 22, 2020); and U.S. patent application Ser. No. 16/855,573 (titled SYSTEM AND METHOD FOR NAVIGATION and filed Apr. 22, 2020), each of which are incorporated by referenced herein in their entirety. Similarly, magnetic distortions may be removed by disclosed methods in U.S. patent application Ser. No. 16/855,487; U.S. patent application Ser. No. 16/855,521; and U.S. patent application Ser. No. 16/855,573. In addition, magnetic distortions may be reduced at the very low field strengths achievable with inverted-direction EM navigation systems (i.e., systems that use micro-coil transmitters and macro-coil receivers) and/or spread spectrum signaling, as further described herein.

It should be noted that the magnetizations and magnetic permeabilities of ferromagnetic materials change with applied magnetic field strength. Additionally, with respect to EM navigation systems that have one set of macro-coils or sensors, one set of micro-coils or sensors, track over the same range, and/or satisfy relevant temperature constraints, the following also applies: a. The magnetic field strengths used with systems that transmit magnetic fields with macro-coils and receive with micro-coils or sensors, in many cases through pulsed direct current (DC) or sinusoidal very low frequency (VLF) signals, can create magnetic distortions by affecting the magnetization and magnetic permeabilities of ferromagnetic materials in the magnetic field (e.g., coercing large magnetizations of ferromagnetic materials and sampling high magnetic permeabilities); and b. The magnetic field strengths used with inverted direction systems (i.e., systems that transmit with micro-coils and receive with macro-coils), which may include pulsed DC or sinusoidal LF signaling, can create magnetic distortions by affecting the magnetization and magnetic permeabilities of ferromagnetic materials in the magnetic field (e.g., coercing medium magnetizations of ferromagnetic materials and sampling high magnetic permeabilities).

It should also be noted that inverted-direction sinusoidal signaling systems can reduce transmitted magnetic field strengths by a factor of $\frac{1}{10}$ via increasing frequencies by a factor of 10. In addition, inverted-direction pulsed DC signaling systems usually have reduced ranges due to limited dynamic ranges or temperature constraints or both. However, the transmitted magnetic field strengths used with inverted-direction spread spectrum signaling systems have limited effect on ferromagnetic materials. These systems further reduce transmitted magnetic field strengths, coerce very small magnetizations of ferromagnetic materials, sample low magnetic permeabilities, and significantly reduce magnetic distortions. Furthermore, inverted-direction spread spectrum signaling systems dramatically reduce field strengths by a factor of $\frac{1}{100}$ via increasing frequencies by a factor of 10 and frequency bandwidth by a factor of 10 or more.

Accordingly, in comparison to standard direction signaling systems (i.e., macro-coil transmitters and mini/micro-coil receivers), inverted-direction signaling systems (i.e., micro-coil transmitters and macro-coil receivers) can significantly reduce distortions while still maintaining a clinically relevant navigation volume and range. In addition, spread-spectrum signaling may be utilized in an inverted-direction system to transmit signals, correct conductive distortions, and further reduce magnetic distortions while expanding the inverted-direction navigation volume and range, as further described herein. Spread-spectrum signaling may also reduce computational burdens associated with correcting distorted data received from the transmitting coils. A spread spectrum system, such as frequency hopping, may include modulation and demodulation of a selected signal, and selected transforms of a signal to confirm or eliminate distortion or distorted signals within the system. Thus, the navigation system may incorporate a spread spectrum system to confirm or determine a signal.

Accordingly, in some embodiments, an EM navigation system may include a transmitting coil array comprising a plurality of transmitting micro coils each attached to an individual vertebra of a spinal column. The transmitting micro coils may receive a signal from a signal generator of a coil array controller. In some embodiments, the signal may be a low power, spread spectrum signal. Each of the transmitting micro coils may be configured to form a distinct EM field as a portion of a navigation region. A receiver coil array, including receiver coils, may be disposed opposite of the transmitting coil array. The receiver coils may detect field components of each of the EM fields. Data may be transmitted from the receiver coils to a receiver coil array interface and then to a processor of the control unit. The processor may process the data to determine a pose, in multiple degrees of freedom (e.g., three degrees of freedom for position and three degrees of freedom for orientation), of each of the transmitting micro coils relative to adjacent transmitting micro coils.

In some embodiments, a distorter may also be introduced into a navigation region. For instance, the distorter may comprise a surgical instrument used during a corrective surgery. Such a distorter can cause distortion in at least one of the EM fields. The distortion to the EM fields may be reduced by the inverted-direction signaling system and the use of spread spectrum signaling, as further discussed herein. EM fields detected by the receiver coils and corresponding data may also be transmitted to the receiver coil array interface and processor. The processor is configured to process the data and add additional corrections to any distorted fields to assist in determining a non-distorted pose of each of the transmitting micro coils.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

Figure 2A:
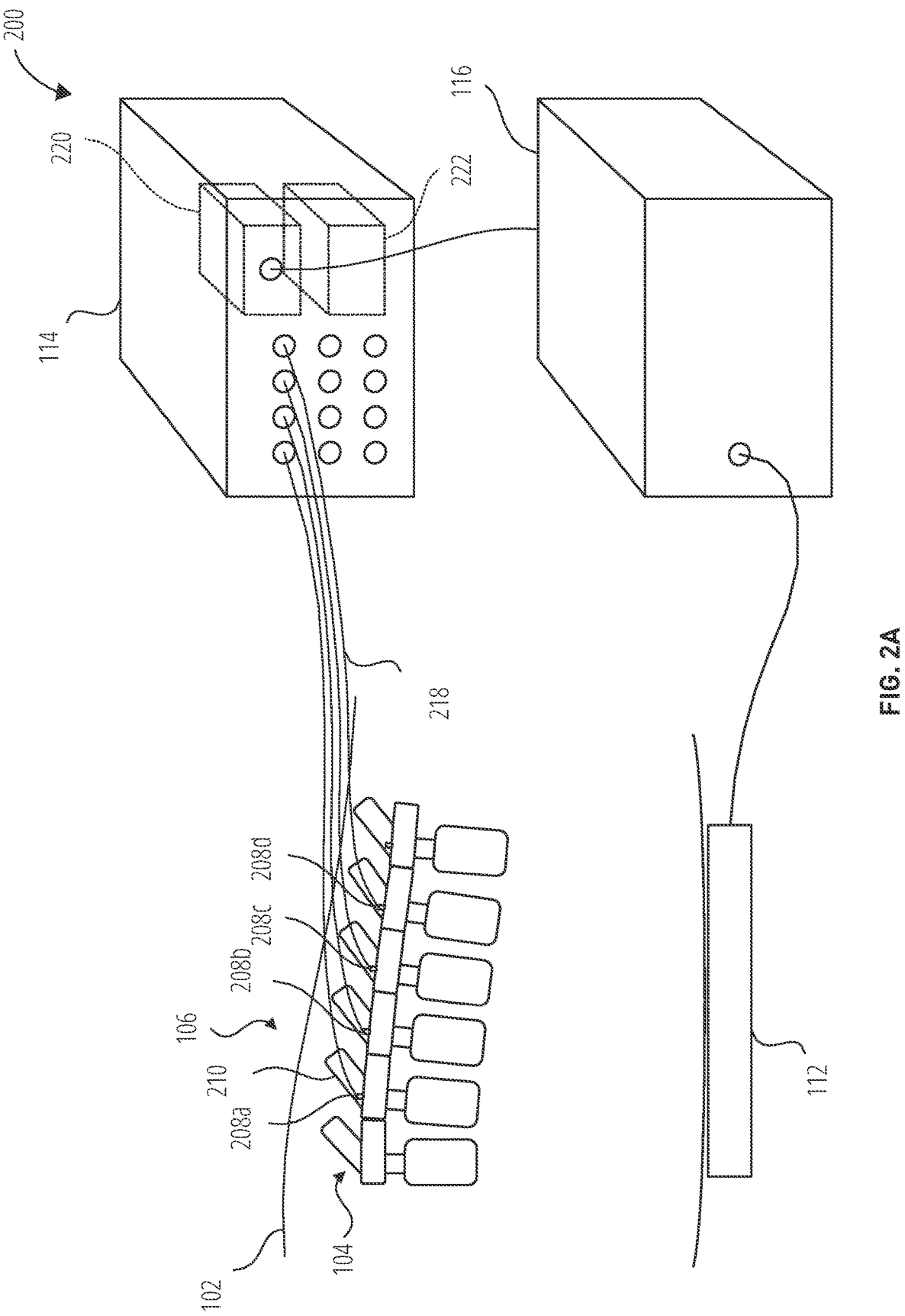
FIG. 2A illustrates an inverted-direction electromagnetic navigation system in accordance with one embodiment.
Figure 2B:
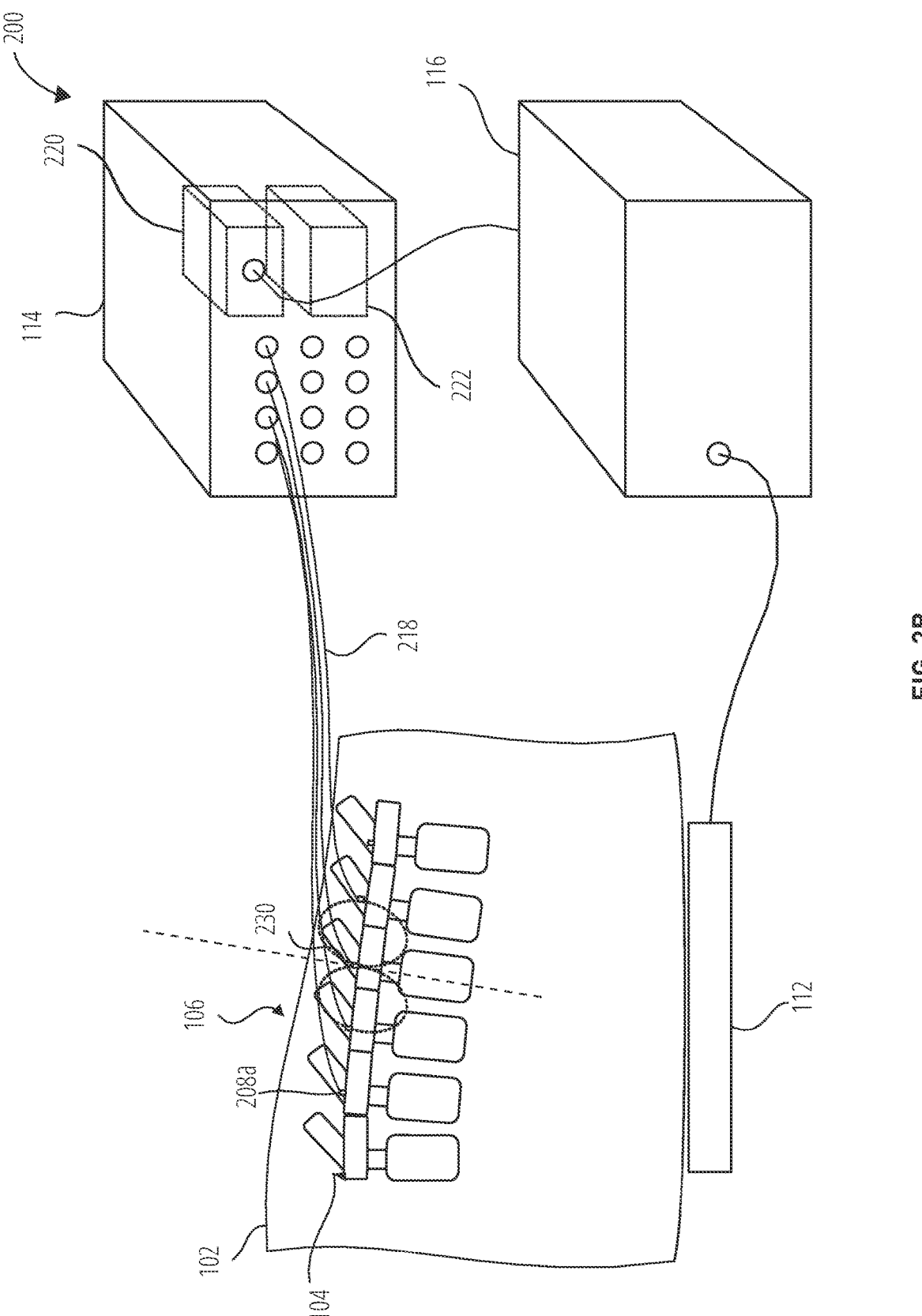
FIG. 2B illustrates an inverted-direction electromagnetic navigation system in accordance with one embodiment.

FIGS. 1-2B illustrate different views of an EM navigation system and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 illustrates an inverted-direction EM navigation system 100 for use in tracking one or more poses of portions of an anatomical structure (e.g., a spinal column or head of an individual) during a corrective surgical procedure (e.g., a spinal corrective surgical procedure). FIG. 1 depicts a spinal column 104 of a patient 102 in a prone position. As illustrated, the EM navigation system 100 may include a transmitter coil array 106, a receiver coil array 112, a coil array controller 114, a receiver coil array interface 116, and a display device 128.

The transmitter coil array 106 comprises a series of transmitting coils coupled to a spinal column 104 of the patient 102, as further described with respect to FIG. 2A. Each of the transmitting coils of the transmitter coil array 106 (and/or the receiver coils of the receiver coil array 112) may comprise conductive material formed or placed in a coil around a permeable core. The coil array controller 114 may be coupled to the transmitter coil array 106. More particularly, the coil array controller 114 may be configured to signal the transmitter coil array 106 to cause the transmitter coil array 106 (and each of the coils within it) to generate or form an electro-magnetic field by driving current through the coils of the transmitter coil array 106, as further shown in FIG. 2B. As the current is driven through the coils, the generated electro-magnetic fields will extend away from the coils and form a navigation domain or volume, such as encompassing all or a portion of a head, spinal column, or other appropriate portion.

Accordingly, each of the transmitting coils (i.e., transmitting micro coils 208a-208d) of the transmitter coil array 106 is configured to generate an EM field that is sensed by the receiver coil array 112, which may be positioned opposite the transmitter coil array 106 on the patient's chest or abdomen, in some embodiments. In other embodiments, the receiver coil array 112 may be positioned at any location adjacent to the patient 102 that is within range to detect the distinct generated EM fields of the transmitting micro coils of the transmitter coil array 106, as further shown and discussed with respect to FIG. 2B. For instance, the receiver coil array 112 may be included within a surgical tool (or tracking device) that is used during an applicable surgical procedure. Notably, the receiver coil array 112 may also include a series of one or more coils comprising conductive material and arranged to receive multiple EM field components with particular geometries.

The receiver coil array interface 116 may be coupled to the receiver coil array 112 and be configured to assist the receiver coil array 112 in determining the pose of transmitting micro coils (e.g., 208 in FIG. 2) and/or the anatomical structures to which they are attached (e.g., vertebra) during corrective surgical procedures. The display device 128 may comprise an display system that is configured to render an image of a target of the procedure (e.g., the spinal column, the head, and so forth). In addition, the display device 128 may analyze and display imaging information (and/or model derived from imaging information) from any type of applicable imaging system, including but not limited to a magnetic resonance imaging (MRI) system, a fluoroscopy imaging system, a computed tomography system, and so forth, in some embodiments. Accordingly, the display device 128 may include a graphical user interface (GUI) that is capable of rendering the targeted anatomical structure in real-time. In addition, the display device 128 may be capable of overlaying multiple rendered images based on imaging information from multiple corresponding imaging systems at a single time. Each of the coil array controller 114, the receiver coil array interface 116, and the display device 128 may also be embodied, for example, by the computing system 400, as further described with respect to FIG. 4.

Notably, more general details associated with EM navigation systems, including the generation of EM fields using transmitting coils and the tracking of such fields by receiving coils, are further outlined and discussed in U.S. application Ser. No. 15/963,444, titled POSITION DETERMINATION SYSTEM AND METHOD and filed Apr. 26, 2018, which is incorporated by reference herein in its entirety.

FIGS. 2A and 2B illustrate a more specific view of an inverted-direction EM navigation system 200 (e.g., the EM navigation system 100 of FIG. 1). As shown in FIG. 2A, the EM navigation system 200 includes the patient 102, spinal column 104, transmitter coil array 106, transmitting micro coils 208 (i.e., transmitting micro coil 208a through transmitting micro coil 208d), a vertebra 210, the receiver coil array 112, the coil array controller 114, the receiver coil array interface 116, lead wires 218, a processor 220, and a signal generator 222. Notably, the configuration of the EM navigation system 200 (and EM navigation system 100) are for example purposes only and may include more or less than the included entities (e.g., the coil array controller 114, the receiver coil array interface 116, and so forth).

As illustrated, the transmitter coil array 106 may be attached to the spinal column 104 of the patient 102. Notably, while the transmitter coil array 106 is shown being utilized with respect to a spinal column, the transmitter coil array 106 and the principles described herein are not limited to such an example and may be practiced with respect to any applicable anatomical structure (e.g., the skull, knees, shoulder, other joints, heart chambers, lungs), or non-anatomical structures outside of the medical field.

As briefly described with respect to FIG. 1, the transmitter coil array 106 may comprise a plurality of transmitting micro coils 208 (e.g., transmitting micro coil 208a through transmitting micro coil 208d) that are each configured to generate distinct electromagnetic fields into a navigation region or patient space of the patient 102 (as further described with respect to FIG. 2B). Each transmitting micro coil 208 is coupled to and disposed on an individual vertebra (e.g., the vertebra 210) of the spinal column 104. While four transmitting micro coils 208 (i.e., transmitting micro coil 208a through transmitting micro coil 208d) are shown in FIGS. 2A and 2B, any number of transmitting micro coils may be utilized in a transmitter coil array (e.g., transmitter coil array 106). In an example, a transmitter coil array may include up to 24 transmitting micro coils. In another example, a transmitter coil array may include as few as one transmitting micro coils.

In some embodiments, each transmitting micro coil 208 may comprise conductive material formed or placed in a coil of about 2 millimeters (mm) in length and about 0.2 mm in outer diameter (OD). In other embodiments, each transmitting micro coil 208 may comprise a coil of about 6 mm OD and about 0.5 mm in length. In yet other embodiments, each transmitting micro coil 208 may comprise a coil of between about 1 mm and 10 mm in its largest dimension. In addition, each of the transmitting micro coils 208 may be coupled to any posterior aspect of a corresponding individual vertebra (e.g., vertebra 210). For instance, each transmitting micro coil 208 may be coupled to the transverse process or the spinous process of a given vertebra (e.g., the vertebra 210). Such coupling of the transmitting micro coils 208 to individual vertebra 210 (or another applicable anatomical structure) may utilize any suitable technique, such as gluing, insertion into a bore hole, and so forth.

In the illustrated embodiment of FIG. 2A, each of the lead wires 218 is attached to a corresponding one of the transmitting micro coils 208 at a first end and operably coupled to the coil array controller 114 at a second end. The lead wires 218 are configured to carry a signal generated at the coil array controller 114 to the transmitting micro coils 208. Notably, the coil array controller may provide generated signals to the plurality of transmitting micro coils in a direct or indirect manner. For instance, the controller may provide signals to the micro coils directly via lead wires 218 or indirectly via wireless communication from the controller to electronics local and connected to the micro coils 208 so that no lead wires are needed.

The coil array controller 114 (and the signal generator 222) may be configured to control and/or drive the transmitter coil array 106 (and each of the transmitting micro coils 208). In addition, as shown, the coil array controller 114 may include the signal generator 222, which is configured to generate and transmit a signal to the transmitting micro coils 208. The coil array controller 114 (and the signal generator 222) may signal each transmitting micro coil 208 in the transmitter coil array 106 in a time division multiplex, a frequency division multiplex, or a code division multiplex manner. In this regard, each transmitting micro coil 208 may be driven separately at a distinct time or all of the transmitting micro coils 208 may be driven simultaneously with each being driven by a different frequency, a plurality of frequencies, or a spread spectrum of frequencies with orthogonal or near orthogonal codes.

The use of a spread spectrum system (with the inverted-direction EM navigation system 200), such as frequency hopping, may include modulation and demodulation of a selected signal, and selected transforms of a signal to further confirm or eliminate distortion or distorted signals within the system. Thus, the EM navigation system 200 may incorporate a spread spectrum system to confirm distortion or eliminate/reduce distortion from a signal. In particular, conductive distortion is dependent on frequencies and includes a phase offset. As such, utilizing spread spectrum signaling (or even multiple different frequencies) allows for determining the phase offsets or impulse response of the distortions for as many different frequencies that are used. For instance, four different frequencies may allow for determining four different offsets. In this way, the distortions can be identified and removed.

In addition, spread spectrum signaling can improve the range of the transmitting micro coils of an inverted-direction EM navigation system, which transmitting micro coils operate at relatively low power (1 mW of transmit coil heat). In particular, the range of a coil is proportion to the signal to noise and noise is equal to the variance of a received signal. As described in U.S. patent application Ser. No. 16/855,487; U.S. patent application Ser. No. 16/855,521; and U.S. patent application Ser. No. 16/855,573—spread spectrum signaling can improve the signal to noise, thereby improving the range of a transmitting micro coil.

Such a spread spectrum transmission is spread across a large or broad frequency spectrum or over a large or broad frequency spectrum which may also be segmented due to time. For example, a spread spectrum signal may transmit a signal across a spectrum of about 1 kilohertz (kHz) to about 400 kHz. In another example, a spread spectrum signal may transmit a signal across a spectrum of about 1 Hz to 30 megahertz (MHz), including about 10 Hz to about 400 kHz that is transmitted at a sample rate at or about 375 kHz. In yet another example, when using multiple frequencies, the signal transmitted may comprise any appropriate frequency range around 200 kHz (e.g., a range including 190 kHz, 195 kHz, 200 kHz, 205 kHz, and so forth). In some embodiments, the frequency range of such multiple frequencies comprises any frequency that is within 100 kHz above or below 200 kHz (i.e., a range of between 100 kHz to 300 kHz). In some embodiments, the frequency range of such multiple frequencies may span across 10 kHz to 400 kHz. Notably, the utilization of spread spectrum signaling is also discussed more specifically, in U.S. patent application Ser. No. 16/855,487; U.S. patent application Ser. No. 15/963, 444; and U.S. patent Ser. No. 16/855,521.

The coil array controller 114 may also include the processor 220. The processor 220 may be configured to receive and process data received at the receiver coil array 112/ receiver coil array interface 116 to determine a pose associated with each of the transmitting micro coils 208. In particular, the processor 220 may be configured to intelligently analyze (e.g., using machine learning or artificial intelligence) data received at the receiver coil array 112/ receiver coil array interface to correct or reduce distortion of the EM fields created by the transmitting micro coils 208. Notably, the processor 220 may also be embodied by the processors(s) 402 as further described with respect to FIG. 4.

As shown in FIG. 2B, upon signaling the transmitting micro coils 208 of the transmitter coil array 106 with the coil array controller 114, a distinct EM field 230 is generated by each transmitting micro coil 208 within the area where a medical procedure is being performed (note only one magnetic field generated by the transmitting micro coil 208c is shown here). The EM fields 230 generated may induce voltages and currents in the coil(s) of the receiver coil array 112. Notably, the receiver coil array comprises at least one receiving coil, which receiving coil may comprise conductive material formed or placed in a coil of between about 10 mm to 60 mm OD. In other embodiments, receiving coils of the receiver coil array may comprise coils of about 54 mm OD and about 7 mm in length. The induced signals from the receiver coil array 112 are delivered to the receiver coil array interface 116 and subsequently forwarded to the processor 220 of the coil array controller 114. The receiver coil array interface 116 may include amplifiers, filters and buffers for directly interfacing with the receiver coils of the receiver coil array 112. Alternatively, the receiver coil array 112 may employ a wireless communications channel as opposed to being coupled directly to the receiver coil array interface 116.

Accordingly, the inverted-direction EM navigation system 200 (and the EM navigation system 100) is configured to determine a pose of anatomical structures (e.g., a given vertebra) by placing the transmitter coil array 106 within/ adjacent to the site of the medical procedure (e.g., on a plurality of vertebrae during a spinal correction surgery) to generate a low-energy EM field associated with each transmitting micro coil 208 of the transmitter coil array 106. A unique set of field components associated with each transmitting micro coil 208 may then be detected/tracked by the receiver coil array 112 and receiver coil array interface 116 to ultimately determine the pose of each of the transmitting micro coils 208 (and the anatomical structure upon which each coil is placed) by measuring the field components at the receiver coil(s) of the receiver coil array 112.

When in use, for example during corrective spinal surgery, the EM navigation system 200 (and the EM navigation system 100) can track the pose of each vertebra 103 of the patient's vertebrae 102 that is being repositioned by a clinician to treat a disease of the patient 102, such as scoliosis. By tracking the pose of each vertebra 210, the clinician can properly locate each vertebra relative to an adjacent vertebra while spinal implants are being implanted. The EM navigation system 200 (and the EM navigation system 100) may track the pose of each vertebra 210 in multiple degrees of freedom, including translation, angle, pitch, yaw, and rotation. The pose of each vertebra 210 may also be displayed on the display device 128 in real-time.

Often when utilizing an EM navigation system, a distorter member may be introduced into the EM navigation system. For instance, a distorter member may comprise a surgical tool/device used during the surgical procedure that utilizes the EM navigation system. In the illustrated embodiment, the surgical instrument acting as distorter member may comprise a ferrous material. In other embodiments, the distorter member may be any object that comprises a ferrous material.

When inserted into an EM navigation system environment, a distorter member may cause a distortion of at least one of the EM fields. In particular, both magnetic distortions (or coerced distortions) and conductive distortions (or induced distortions) may occur within an environment of an EM navigation system. Such distortions can be especially problematic in standard direction signaling EM navigation systems by causing distorted tracking of generated EM fields at receiver coil arrays. However, inverted-direction EM navigation systems, such as the EM navigation system 200 described herein can greatly reduce such distortions. In addition, spread spectrum signaling (or even multiple frequencies) may be utilized in such inverted-direction EM navigation systems to reduce and/or correct distortions (e.g., by allowing for identifying phase offsets or impulse responses). In addition, spread spectrum signaling may be utilized in such inverted-direction EM navigation systems to increase a transmitting coils range by increasing signal to noise, as described in U.S. patent application Ser. No. 16/855,487; U.S. patent application Ser. No. 16/855,521; and U.S. patent application Ser. No. 16/855,573.

FIG. 3 illustrates a flowchart of a method 300 for tracking a pose of a portion of an anatomical structure (e.g., a vertebra of a spinal column) using an inverted-direction electromagnetic navigation system In block 302, the method 300 generates a signal comprising a plurality of frequencies. For instance, the signal generator 222 of the coil array controller 114 may generate a signal comprising spread spectrum signaling. In block 304, the method 300 receives the signal comprising the plurality of frequencies at a transmitter coil array. For instance, the spread spectrum signaling may be received at the transmitting micro coils 208. In addition, the transmitter coil array may comprise a plurality of transmitting micro coils and each of the plurality of transmitting micro coils may be coupled to a portion of an anatomical structure (e.g., a vertebra of a spinal column) of a patient.

In block 306, the method 300, in response to receiving the signal comprising the plurality of frequencies, generates an electromagnetic field at each of the plurality of transmitting micro coils based on the received signal. For instance, each of the transmitting coils in the ongoing example may generate an electromagnetic field based on the received spread spectrum signaling. In block 308, the method 300 detects each of the generated electromagnetic field components at a receiver coil array comprising at least one receiving coil and more generally a plurality of receiving coils. For instance, the receiver coil array 112 may detect each of the generated electromagnetic field components and provide information associated with such detection to the receiver coil array interface 116. In block 310, the method 300 determines a pose of at least one of the plurality of transmitting micro coils. For instance, the receiver coil array interface 116 and/or the processor 220 may utilize such received information from the receiver coil array 112 to determine a pose of at least one vertebra 210/transmitting micro coil 208.

In this way, inverted-direction EM navigation systems (i.e., micro transmitting coils and macro receiving coils) can significantly reduce distortions while providing clinically relevant useful navigation volume and range. In addition, spread spectrum signaling (or use of multiple frequencies) within the inverted-direction EM may allow for correcting conductive distortions, and further reducing magnetic distortions while expanding the inverted-direction navigation volume and range.

Notably, while the novel tracking aspects described herein are generally described with respect to the medical field, these principles may also be utilized in various other fields. In particular, these principles may be practiced in any field or area that could benefit from high accuracy identification of position and/or orientation of a tracked structure. For instance, shipping logistics (e.g., tracking crates), automated "pick-and-place" type operations (e.g., AMAZON® warehouses), augmented reality (AR) applications (e.g., tracking a surgeon's AR headset), robotic applications, and so forth.

Some general discussion of a computing system will now be described with respect to FIG. 4. Computing systems are now increasingly taking a wide variety of forms. Computing systems may, for example, be handheld devices, appliances, laptop computers, desktop computers, mainframes, distributed computing systems, datacenters, or even devices that have not conventionally been considered a computing system, such as wearables (e.g., glasses, smart watches, and so forth). In this description and in the claims, the term "computing system" is defined broadly as including any device or system (or combination thereof) that includes at least one physical and tangible processor, and a physical and tangible memory capable of having thereon computer-executable instructions that may be executed by a processor. The memory may take any form and may depend on the nature and form of the computing system. A computing system may be distributed over a network environment and may include multiple constituent computing systems.

Figure 4:
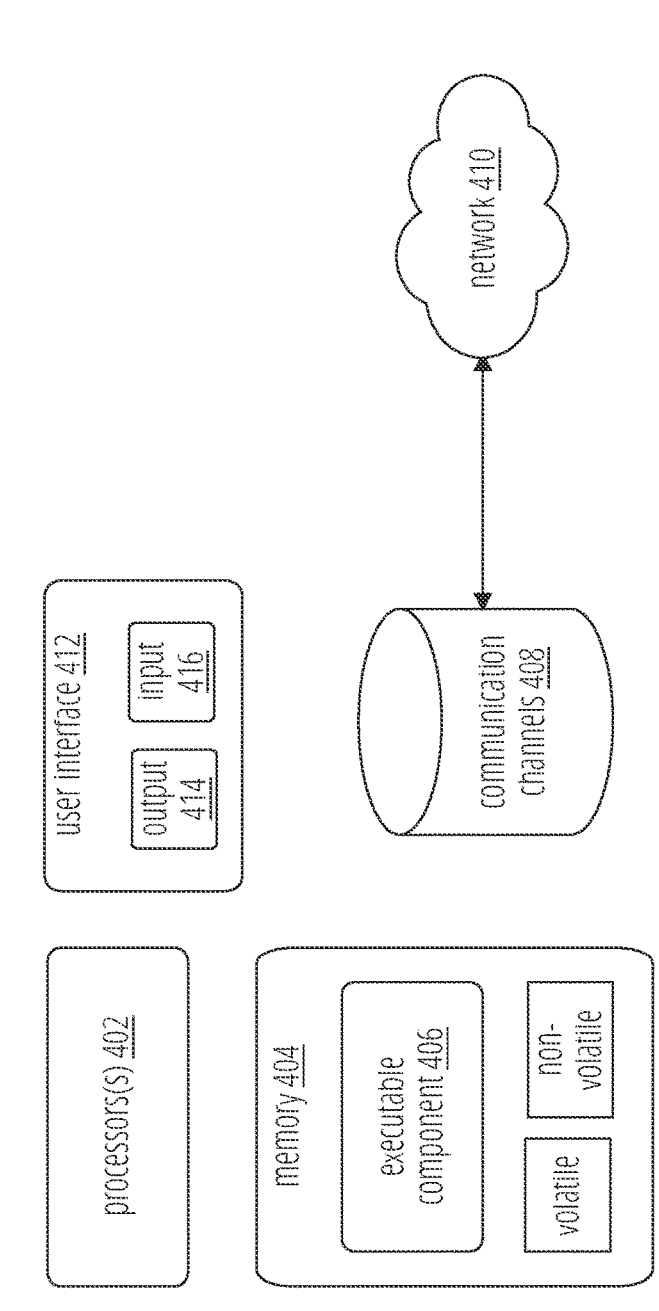
FIG. 4 illustrates an example computer architecture that facilitates operation of the principles described herein.

As illustrated in FIG. 4, in its most basic configuration, a computing system 400 typically includes at least one hardware processing unit 102 (or processors(s) 402 and memory 404. The memory 404 may be physical system memory, which may be volatile, non-volatile, or some combination of the two. The term "memory" may also be used herein to refer to non-volatile mass storage such as physical storage media. If the computing system is distributed, the processing, memory and/or storage capability may be distributed as well.

The computing system 400 also has thereon multiple structures often referred to as an "executable component." For instance, the memory 404 of the computing system 400 is illustrated as including executable component 406. The term "executable component" is the name for a structure that is well understood to one of ordinary skill in the art in the field of computing as being a structure that can be software, hardware, or a combination thereof. For instance, when implemented in software, one of ordinary skill in the art would understand that the structure of an executable component may include software objects, routines, methods, and so forth, that may be executed on the computing system, whether such an executable component exists in the heap of a computing system, or whether the executable component exists on computer-readable storage media.

In such a case, one of ordinary skill in the art will recognize that the structure of the executable component exists on a computer-readable medium such that, when interpreted by one or more processors of a computing system (e.g., by a processor thread), the computing system is caused to perform a function. Such structure may be computer-readable directly by the processors (as is the case if the executable component is binary). Alternatively, the structure may be configured to be interpretable and/or compiled (whether in a single stage or in multiple stages) so as to generate such binary that is directly interpretable by the processors. Such an understanding of example structures of an executable component is well within the understanding of one of ordinary skill in the art of computing when using the term "executable component".

The term "executable component" is also well understood by one of ordinary skill as including structures that are implemented exclusively or near-exclusively in hardware, such as within a field programmable gate array (FPGA), an application specific integrated circuit (ASIC), a central processing unit (CPU), a graphics processing unit (GPU), or any other specialized circuit. Accordingly, the term "executable component" is a term for a structure that is well understood by those of ordinary skill in the art of computing, whether implemented in software, hardware, or a combination. In this description, the terms "component", "service", "engine", "module", "control", or the like may also be used. As used in this description and in the case, these terms (whether expressed with or without a modifying clause) are also intended to be synonymous with the term "executable component", and thus also have a structure that is well understood by those of ordinary skill in the art of computing.

In the description that follows, embodiments are described with reference to acts that are performed by one or more computing systems. If such acts are implemented in software, one or more processors (of the associated computing system that performs the act) direct the operation of the computing system in response to having executed computer-executable instructions that constitute an executable component. For example, such computer-executable instructions may be embodied on one or more computer-readable media that form a computer program product. An example of such an operation involves the manipulation of data.

The computer-executable instructions (and the manipulated data) may be stored in the memory 404 of the computing system 400. Computing system 400 may also contain communication channels 408 that allow the computing system 400 to communicate with other computing systems over, for example, network 410.

While not all computing systems require a user interface, in some embodiments, the computing system 400 includes a user interface 412 for use in interfacing with a user. The user interface 412 may include output 414 (or output mechanism(s) 114) as well as input 416 (or input mechanism(s) 116). The principles described herein are not limited to the precise type of output 414 or type of input 416 as such will depend on the nature of the device. However, output 414 might include, for instance, speakers, displays, tactile output, holograms and so forth. Examples of input 416 might include, for instance, microphones, touchscreens, holograms, cameras, keyboards, mouse of other pointer input, sensors of any type, and so forth.

Embodiments described herein may comprise or utilize a special purpose or general-purpose computing system including computer hardware, such as, for example, one or more processors and system memory, as discussed in greater detail below. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: storage media and transmission media.

Computer-readable storage media includes RAM, ROM, EEPROM, CD-ROM or other optical disk storage, magnetic disk storage or other magnetic storage devices, or any other physical and tangible storage medium which can be used to store desired program code means in the form of computer-executable instructions or data structures and which can be accessed by a general purpose or special purpose computing system.

A "network" (e.g., the network 410) is defined as one or more data links that enable the transport of electronic data between computing systems and/or modules and/or other electronic devices. When information is transferred or provided over a network or another communications connection (either hardwired, wireless, or a combination of hardwired or wireless) to a computing system, the computing system properly views the connection as a transmission medium. Transmissions media can include a network and/or data links which can be used to carry desired program code means in the form of computer-executable instructions or data structures and which can be accessed by a general purpose or special purpose computing system. Combinations of the above should also be included within the scope of computer-readable media.

Further, upon reaching various computing system components, program code means in the form of computer-executable instructions or data structures can be transferred automatically from transmission media to storage media (or vice versa). For example, computer-executable instructions or data structures received over a network or data link can be buffered in RAM within a network interface module (e.g., a "NIC"), and then eventually transferred to computing system RAM and/or to less volatile storage media at a computing system. Thus, it should be understood that storage media can be included in computing system components that also (or even primarily) utilize transmission media.

Computer-executable instructions comprise, for example, instructions and data which, when executed at a processor, cause a general purpose computing system, special purpose computing system, or special purpose processing device to perform a certain function or group of functions. Alternatively, or in addition, the computer-executable instructions may configure the computing system to perform a certain function or group of functions. The computer executable instructions may be, for example, binaries or even instructions that undergo some translation (such as compilation) before direct execution by the processors, such as intermediate format instructions such as assembly language, or even source code.

Those skilled in the art will appreciate that the invention may be practiced in network computing environments with many types of computing system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, datacenters, wearables (such as glasses) and the like. The invention may also be practiced in distributed system environments where local and remote computing systems, which are linked (either by hardwired data links, wireless data links, or by a combination of hardwired and wireless data links) through a network, both perform tasks. In a distributed system environment, program modules may be located in both local and remote memory storage devices.

Those skilled in the art will also appreciate that the invention may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An inverted-direction electromagnetic (EM) navigation system, comprising:

a transmitter coil array comprising a plurality of transmitting micro coils that are between 1 millimeter (mm) to 10 mm in their largest size, each of the plurality of transmitting micro coils configured to be separately coupled to a portion of a tracked structure;

a coil array controller configured to couple to each of the plurality of transmitting micro coils and configured to generate a signal comprising a plurality of frequencies and provide the generated signal to each of the plurality of transmitting micro coils, wherein the generated signal is configured to cause each of the plurality of transmitting micro coils to generate, radiate and emit a corresponding EM field based on the generated signal, where each corresponding EM field is a distinct EM field as a portion of a navigation region; and a receiver coil array comprising at least one receiving macro coil that is between 10 mm to 60 mm in its largest size, the receiver coil array configured to detect the corresponding distinct generated, radiated and emitted EM field from each of the plurality of transmitting micro coils to thereby determine a pose of each of the plurality of transmitting micro coils in the navigation region;

wherein the plurality of frequencies comprises a spread spectrum of frequencies, wherein the generated, radiated and emitted EM field created by each one of the plurality of transmitting micro coils comprises a generated, radiated and emitted spread spectrum EM field sensed by the at least one receiving macro coil; and wherein each of the transmitting micro coils is smaller than the at least one receiving macro coil.

2. The electromagnetic navigation system of claim 1, wherein the spread spectrum of frequencies range from 1 kilohertz (kHz) to 400 kHz.

3. The electromagnetic navigation system of claim 1, wherein each of the plurality of frequencies comprises a frequency between 10 kHz and to 400 kHz.

4. The electromagnetic navigation system of claim 1, wherein each transmitting micro coil of the plurality of transmitting micro coils is configured to be attached to an individual vertebra of a spinal column.

5. The electromagnetic navigation system of claim 1, wherein the spread spectrum of frequencies comprises a frequency range of 1 Hz to 30 MHz with 10 Hz to 400 kHz of the frequency spectrum transmitted at a sample rate of 375 kHz.

6. The electromagnetic navigation system of claim 1, wherein the spread spectrum of frequencies comprises a frequency range of 100 kHz to 300 KHz.

7. The electromagnetic navigation system of claim 1, wherein the coil array controller is further configured to simultaneously drive each transmitting micro coil with the spread spectrum of frequencies.

8. The electromagnetic navigation system of claim 1, wherein coil array controller is further configured to separately drive at a distinct time each transmitting micro coil with the spread spectrum of frequencies.

9. A method of tracking a pose of a tracked structure using an inverted-direction electromagnetic (EM) navigation system, comprising:

generating a signal comprising a plurality of frequencies;

receiving the signal comprising the plurality of frequencies at a transmitter coil array, the transmitter coil array comprising a plurality of transmitting micro coils, each of the plurality of transmitting micro coils being coupled individually to a portion of a tracked structure;

in response to receiving the signal comprising the plurality of frequencies, generating, radiating and emitting an EM field at each of the plurality of transmitting micro coils based on the received signal, where each of the corresponding EM field is a distinct EM field as a portion of a navigation region;

detecting each of the distinct generated, radiated and emitted EM fields at a receiver coil array comprising at least one receiving macro coil; and determining a pose of each of the plurality of transmitting micro coils in the navigation region;

wherein the EM field generated, radiated and emitted at each one of the plurality of transmitting micro coils comprises a generated, radiated and emitted spread spectrum EM field sensed by the at least one receiving macro coil, wherein the spread spectrum EM field comprises a spread spectrum of frequencies of 1 Hz to 30 MHz with 10 Hz to 400 kHz of the spread spectrum of frequencies transmitted at a sample rate of 375 kHz; and wherein each of the transmitting micro coils is smaller than the at least one receiving macro coil.

10. The method of claim 9, wherein the spread spectrum of frequencies range from 1 kilohertz (kHz) to 400 kHz.

11. The method of claim 9, wherein each frequency of the spread spectrum of frequencies comprises a frequency between 10 kHz to 400 kHz.

12. The method of claim 9, wherein the plurality of transmitting micro coils are between 1 millimeter (mm) to 10 mm in their largest size.

13. The method of claim 9, wherein the at least one receiving macro coil is between 10 mm to 60 mm in their largest size.

14. A computer program product comprising one or more non-transitory computer readable medium having stored thereon computer-executable instructions that are executable by one or more processors of a computing system to cause the computing system to track a pose of a tracked structure using an inverted-direction electromagnetic (EM) navigation system, the computer-executable instructions including instructions that are executable to cause the computing system to perform at least the following:

generate a signal comprising a plurality of frequencies;

send the signal comprising the plurality of frequencies to a transmitter coil array, the transmitter coil array comprising a plurality of transmitting micro coils that are between 1 millimeter (mm) to 10 mm in their lamest size, each of the plurality of transmitting micro coils being coupled separately to a portion of a tracked structure, wherein the transmitter coil array generates, radiates and emits an EM field at each of the plurality of transmitting micro coils based on the received signal, where each of the corresponding EM field is a distinct EM field as a portion of a navigation region;

detect each of the distinct generated, radiated and emitted EM fields via a receiver coil array comprising at least one receiving macro coil that is between 10 mm to 60 mm in its largest size; and determine a pose of each of the plurality of transmitting micro coils in the navigation region;

wherein the plurality of frequencies comprises a spread spectrum of frequencies, wherein the generated, radiated emitted EM field created at each one of the plurality of transmitting micro coils comprises a generated, radiated and emitted spread spectrum EM field sensed by the at least one receiving macro coil; and wherein each of the transmitting micro coils is smaller than the at least one receiving macro coil.

15. The computer program product of claim 14, wherein the spread spectrum of frequencies range from 1 kilohertz (kHz) to 400 kHz.

16. The computer program product of claim 14, wherein each of the plurality of frequencies comprises a frequency between 10 kHz to 400 KHz.

17. The computer program product of claim 14, wherein each transmitting micro coil of the plurality of transmitting micro coils is configured to be attached to an individual vertebra of a spinal column.

18. The computer program product of claim 14, wherein the spread spectrum of frequencies comprises a frequency range of 1 Hz to 30 MHz with 10 Hz to 400 kHz of the frequency spectrum transmitted at a sample rate of 375 kHz.

19. The computer program product of claim 14, wherein the spread spectrum of frequencies comprises a frequency range of 100 kHz to 300 KHz.

20. The computer program product of claim 14, wherein the signal sent to the transmitter coil array is configured to simultaneously drive each transmitting micro coil with the plurality of frequencies.

* * * * *